(12) United States Patent
Ravenscroft

(10) Patent No.: US 6,773,453 B2
(45) Date of Patent: *Aug. 10, 2004

(54) METHOD AND APPARATUS FOR INTRALUMINALLY IMPLANTING AN ENDOVASCULAR AORTIC GRAFT

(75) Inventor: Adrian C. Ravenscroft, Lower Mills, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/145,168

(22) Filed: May 13, 2002

(65) Prior Publication Data

US 2002/0128703 A1 Sep. 12, 2002

Related U.S. Application Data

(60) Continuation of application No. 09/378,268, filed on Aug. 20, 1999, now Pat. No. 6,432,131, which is a continuation of application No. 09/060,950, filed on Apr. 15, 1998, now Pat. No. 6,016,810, which is a division of application No. 08/381,099, filed on Jan. 31, 1995, now Pat. No. 5,755,770.

(51) Int. Cl.[7] ................................................. A61F 2/06
(52) U.S. Cl. ..................................... 623/1.13; 623/1.15
(58) Field of Search .............................. 623/1.12, 1.13, 623/1.15–1.22, 1.35

(56) References Cited

U.S. PATENT DOCUMENTS

| | | | |
|---|---|---|---|
| 3,657,744 A | * 4/1972 | Ersek | ......................... 128/898 |
| 3,945,052 A | 3/1976 | Liebig | |
| 4,190,909 A | 3/1980 | Ablaza | |
| 4,655,771 A | 4/1987 | Wallsten | |
| 4,728,328 A | 3/1988 | Hughes et al. | |
| 4,733,665 A | 3/1988 | Palmaz | |
| 4,787,899 A | 11/1988 | Lazarus | |
| 5,061,275 A | 10/1991 | Wallstén et al. | |
| 5,104,399 A | 4/1992 | Lazarus | |
| 5,122,154 A | 6/1992 | Rhodes | |
| 5,135,536 A | 8/1992 | Hillstead | |
| 5,219,355 A | 6/1993 | Parodi et al. | |
| 5,366,504 A | 11/1994 | Andersen et al. | |
| 5,425,765 A | 6/1995 | Tiefenbrun et al. | |
| 5,522,881 A | 6/1996 | Lentz | |
| 5,683,452 A | * 11/1997 | Barone et al. | ............... 128/898 |
| 5,693,087 A | 12/1997 | Parodi | |
| 5,693,088 A | 12/1997 | Lazarus | |
| 5,755,770 A | 5/1998 | Ravenscroft | |
| 5,824,053 A | 10/1998 | Khosravi et al. | |
| 5,836,316 A | 11/1998 | Plaia et al. | |
| 5,836,964 A | 11/1998 | Richter et al. | |
| 6,016,810 A | * 1/2000 | Ravenscroft | ................ 128/898 |
| 6,273,910 B1 | 8/2001 | Limon | |
| 6,432,131 B1 | * 8/2002 | Ravenscroft | ............... 623/1.13 |

FOREIGN PATENT DOCUMENTS

EP 0461791 A1 12/1991

OTHER PUBLICATIONS

Supplementary European Search Report from corresponding European application dated Feb. 17, 1999.

* cited by examiner

*Primary Examiner*—Corrine McDermott
*Assistant Examiner*—Hieu Phan
(74) *Attorney, Agent, or Firm*—RatnerPrestia

(57) ABSTRACT

An intraluminal prosthesis for intraluminal repair of body conduits, especially aortic aneurysms, is disclosed. The prosthesis includes a generally tubular, flexible graft (20) having a proximal open end (30) and at least one distal open end (31) terminating in a hem (33). A stent (21) can be disposed within the proximal open end (30) and is adapted to be attached to the body conduit (1). The hem (33) is inverted within the graft so that it is disposed as a cuff (34) within the graft. The hem (33) is arranged so that upon withdrawing the distal open end (31) from inside the cuff (34), the cuff will unfold and follow the distal open end to expose it to receive another stent for attachment to the body conduit (12) for intraluminal implantation of the graft. Preferably the hem is folded a second time within the cuff to form a second cuff (35) within the graft. The stents are preferably formed of a plexus of wires adapted to expand from a first narrow diameter to a second diameter to engage the body conduit. Also disclosed is a method of intraluminal implantation of the graft.

29 Claims, 3 Drawing Sheets

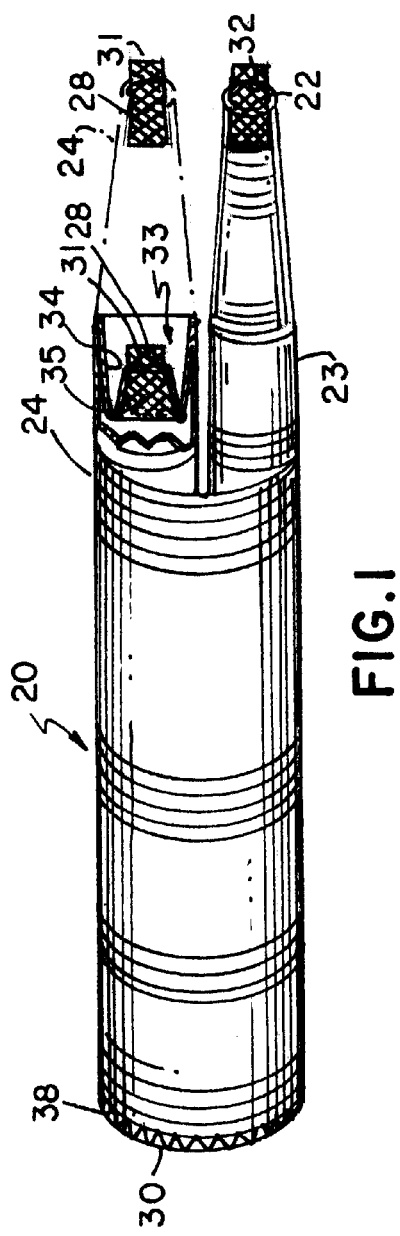
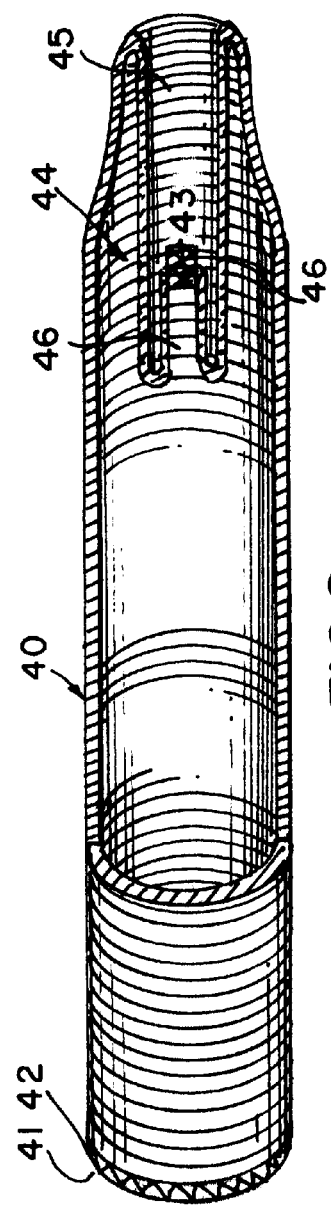
FIG.1
FIG.2

METHOD AND APPARATUS FOR INTRALUMINALLY IMPLANTING AN ENDOVASCULAR AORTIC GRAFT

This application is a continuation of U.S. patent application Ser. No. 09/378,268, filed Aug. 20, 1999 now U.S. Pat. No. 6,432,131; which is a continuation of U.S. patent application Ser. No. 09/060,950, filed Apr. 15, 1998 (which issued on Jan. 25, 2000 as U.S. Pat. No. 6,016,810); which is a divisional of U.S. patent application Ser. No. 08/381,099, filed Jan. 31, 1995 (which issued on May 26, 1998 as U.S. Pat. No. 5,755,770).

FIELD OF THE INVENTION

The present invention relates to an interluminal prosthesis for intraluminal repair of body conduits. More specifically, the present invention relates to intraluminal repair of aneurysms using an arterial interluminal prothesis. Furthermore, the present invention relates to a method of implanting the interluminal prosthesis in an artery. The invention especially relates to an arterial interluminal prosthesis having a tubular form where one end of the tube is connected to the thoracic aorta and the other end is bifurcated to form two tubular passageways and each passageway is connectable to each of the iliac arteries.

DESCRIPTION OF THE PRIOR ART

Interluminal devices for repairing body conduits are well known to the art. Such devices include tubular flexible grafts that are implanted by the use of stents. Stents are a means of attachment of intravascular prostheses.

With special reference to abdominal aortic aneurysms, such aneurysms occur because of an abnormal dilation of the wall of the aorta within the abdomen. Surgical procedures involving the abdominal wall are major undertakings with high associated risk together with considerable mortality. The replacement of the aorta with surgical procedures involves replacing the diseased portion of the vessel with a prosthetic device which is typically formed of a synthetic tube or graft, usually fabricated of Dacron®, Teflon®, or other suitable material. In the surgical procedure, the aorta is exposed through an abdominal incision. The aorta is closed both above and below the aneurysm so that the aneurysm can be opened and any thrombus and arteriosclerotic debris can be removed. A graft of approximately the size of a normal aorta and is sutured in place to replace the aneurysm. Blood flow is then reestablished through the graft. Surgery according to the prior art required an extended recovery period together with difficulties in suturing the graft to the aorta.

In the European patent application to Barone et al., number 0,461,791 A1, a method is disclosed for repairing an abdominal aortic aneurysm which includes a tubular graft that is intraluminally delivered through the iliac artery and secured to the aorta by the expansion and deformation of a stent. In the application, a tube is disclosed which has a single end that is bifurcated to two other ends each of which is attached to one of the iliac arteries. Such disposition of the graft can provide a reduction in the trauma of the surgery because the graft is delivered to the site intraluminally. While one connection to an iliac artery is reasonably easy to accomplish, rather complicated techniques are required to move the other leg of the graft to the other iliac artery and connect it thereto.

A patent to Parodi et al., U.S. Pat. No. 5,219,355, discloses a balloon device for implanting an aortic interluminal prosthesis to repair aneurysms. In the patent, a graft prothesis is disposed upon a catheter having two balloons mounted thereon. The prosthesis is mounted on the catheter and stents are mounted upon the balloons. The assembly of the graft, the two balloons and the stents are introduced into the aneurysm by catheterization. The balloons are inflated to implant the prosthesis within the aneurysm and affix the stents against the artery walls, thereby to repair the aneurysm. The balloons are deflated and the catheter is withdrawn.

SUMMARY OF THE INVENTION

According to the present invention I have discovered an interluminal prothesis especially useful for intraluminal repair of aneurysms. The prothesis includes a generally tubular flexible graft of conventional prosthetic graft material having a proximal open end and at least one leg with a distal open end and preferably two legs with two distal open ends. Preferably, a first stent is disposed within and attached to the proximal open end. The first stent emerges from the proximal open end and is adapted to be attached to the aorta intraluminally. A hem terminating in the distal open end of the graft is inverted within the leg. The hem is arranged as a cuff within the leg. A second stent having a proximal and a distal end can be attached to the interior of the distal end of the cuff so upon withdrawing the second stent from the cuff, the cuff will unfold and follow the stent for implantation of the graft. In a preferred embodiment the graft is bifurcated at one end to form two legs, each terminating in distal open ends. Each leg is attached to one of the iliac arteries. In the preferred embodiment also, the hem is inverted a second time to form a second cuff within the first cuff. The stent extends outwardly from the distal open end of the second cuff. Many of the stents are devices which are deformed by increasing the diameter until they engage a wall of a body conduit and are anchored thereto. Alternatively they may be integrally knitted into the graft or they may be polymeric impregnations of the graft which harden upon heating to enable the hardened impregnation to engage the body conduit.

To dispose the graft within the aorta a conventional guidewire is threaded through the iliac artery into the aorta using conventional techniques. A delivery catheter is then threaded over the guidewire until it reaches the desired location within the aorta. A graft having at least two open ends is disposed on the delivery catheter. Each open end of the graft can have a stent disposed therein. The portion of the graft that is adapted to be attached to the aorta has the stent extending outwardly from its open end so that the graft may be attached to the aorta. In the case of a bifurcated graft in which two legs of the graft are to be attached to the two iliac arteries branching from the aorta, one of the legs can have a stent extending outwardly from its open end. The other leg of the graft is disposed inside the graft leg in the form of a cuff which is inverted into itself at the open end. A stent can be attached to the cuff. A balloon catheter is disposed near the end of the inverted leg. The inside of the inverted leg is engaged by the balloon and is withdrawn through the other iliac artery. When appropriately positioned within the iliac artery, the stent is expanded to engage the artery and set it. The balloon and then the guidewire is then withdrawn from the artery and the procedure is completed.

BRIEF DESCRIPTION OF THE DRAWINGS

FIG. 1 is a side elevational view partially in cross section of one embodiment of a bifurcated aortic implant adapted to be disposed within an aneurysm formed in the aorta and connected to each iliac artery.

FIG. 2 is a side elevational view, partially in cross-section, illustrating another embodiment of an aortic implant.

DESCRIPTION OF THE PREFERRED EMBODIMENTS

Figure 3:
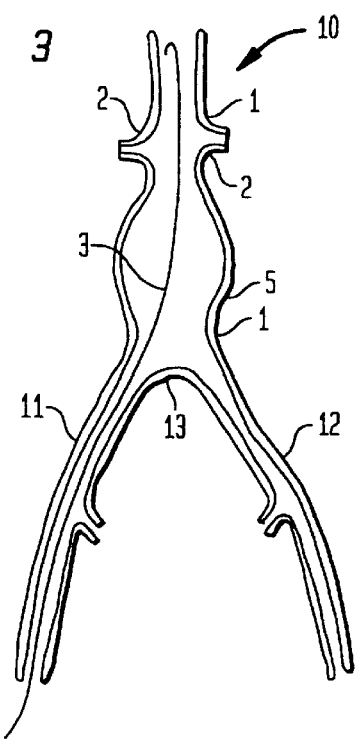
FIGS. 3 to 10 are a series of views showing a stage-wise progression for performing a procedure to implant a graft within an aortic aneurysm.

Referring now to FIG. 1, an arterial interluminal prosthesis 20 for repairing aneurysms is shown, partially in cross section. The graft or prosthesis, when implanted, has a generally circular cross-sectional configuration. It may be made from a variety of materials provided they have requisite strength characteristics to be utilized an aortic graft as well as have requisite compatibility with the human body so that the implant material will not be rejected. Examples of such material are Dacron® and other polyester materials, Teflon® (polytetrafluoroethylene), Teflon® coated with Dacron® material and porous polyethylene urethane. The material can be knitted or woven. The graft can also be made of extruded polymeric materials, all of which are well known to the art as graft materials.

The graft 20 has a proximal open end 30 and two distal open ends 31 and 32. The distal open ends are disposed on legs 23 and 24 which bifurcate from the graft 20. Each leg preferably is the same length initially, although with some procedures it may be preferable to make the legs axially stretchable to provide for adjustments in length which may be needed during implantation. The distal open end 31 of the leg 24 is at the end of a hem 33 which extends from the edge of the inward fold of the leg 24 to the distal open end 31. The length of the leg 24 is not critical so long as it is adequate to be grasped by a catheter and intraluminally drawn into the iliac artery. A first inversion of the hem 33 forms a first cuff 34. In the preferred embodiment the hem 33 is inverted a second time to form a second cuff 35 which opens away from the proximal open end 30. Preferably the leg 24 (or both the legs 24 and 23) are truncated or tapered with the narrowest diameter being at the distal open ends to enable the hem to be more easily folded within the leg and form a cuff(s).

A stent 28 is disposed within the distal open end 31 of graft 20. The stent emerges from the distal open end 31 to enable it to be attached to the iliac artery. Another stent 22 is disposed within the leg 23 at its distal open end 32. A third stent 38 is disposed in the proximal open end 30 to attach to the thoracic artery.

Several types of stents can be used. Common stents are plexuses of wires that can be expanded with internal force, such as provided by a balloon, to engage an artery wall. Other stents having applicability include polymeric expandable structural members and polymeric compositions at the end of the leg which harden when expanded and activated by heat. A stent can alternatively be constructed as a lining within a graft and extending from one end of the graft to the other to provide for both fastening of the graft to an artery and its structural stability.

Referring now to FIG. 2, a graft 40 is shown partially in cross-section. In this embodiment the graft 40 is tubular-shaped and does not have two legs as is disclosed in the previous embodiment. The graft 40 has a proximal open end 41 in which a stent 42 is disposed. The graft 40 further has a distal open end 43 disposed at the end of a hem 44. The hem 44 is inverted within the graft 40 to form a first cuff 45 and in the preferred embodiment is inverted a second time to form a second cuff 46. The second cuff 46 is especially beneficial because it enables the hem 33 to be withdrawn from the leg 24 easily. When a stent is inserted within the distal open end 43 it can engage the distal open end 43 to draw the hem 44 outwardly and cause the cuff 45 to unfold and then cause the cuff 46 to unfold also. In this embodiment, as with the embodiment illustrated in FIG. 1, the graft 40 can be truncated or tapered toward the distal open end to provide for easy inversion of the hem 44 into the graft 40. In the preferred embodiment, the hem is truncated into two progressively narrower diameters or tapered with the distal open end 43 having the smallest diameter.

FIGS. 3 to 10 show a portion of the abdominal aortic artery to be treated connected in its upper part with thoracic artery 1 from which renal arteries 2 depart. The abdominal aorta presents an aneurysm 5 which goes almost to the thoracic aorta 1. The thoracic aorta 1 bifurcates at 13 into two iliac arteries 11 and 12.

A conventional guidewire 3 is conventionally threaded into the right iliac artery 11 into the abdominal aorta through the aneurysm 5 until it reaches the thoracic aorta 1, as shown in FIG. 3.

Figure 4:
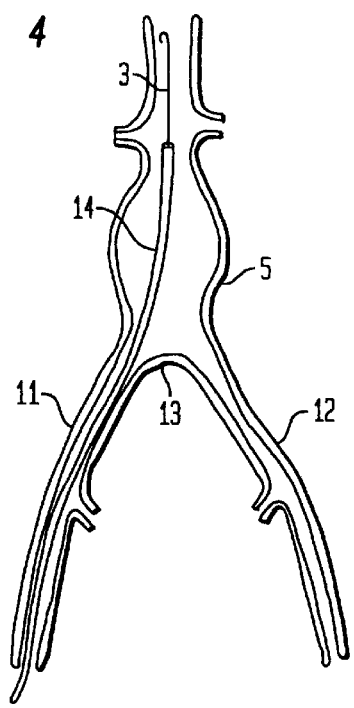

Referring to FIG. 4, implantation of the graft illustrated in FIG. 1 is shown. A delivery catheter covered by a sleeve 14 is slipped over the guidewire 10 until its distal end is located above the aneurysm 5. The delivery catheter includes a hollow center shaft (not shown) covered by the graft as shown in FIG. 1, the graft being tightly wrapped around the delivery catheter, as is conventional. The assembly of the delivery catheter would be the same for the embodiment shown in FIG. 2. If stents are delivered with the graft, they are collapsed, as is conventional also. The graft and stents are covered by the sleeve 14, as is conventional also. After delivery of the graft, it is positioned so that its proximal open end 30 is above the aneurysm 5. The sleeve 14 is withdrawn through the iliac artery 11 to leave the graft and stent uncovered. In the embodiment shown, especially in FIG. 5, as the sleeve 14 is withdrawn through the artery 11, stent 21 will automatically enlarge to engage the aorta wall 1 and as the sleeve 14 is further withdrawn, stent 22 enlarges and engages the interior of artery 11 to anchor the graft 20 in place.

Figure 5:
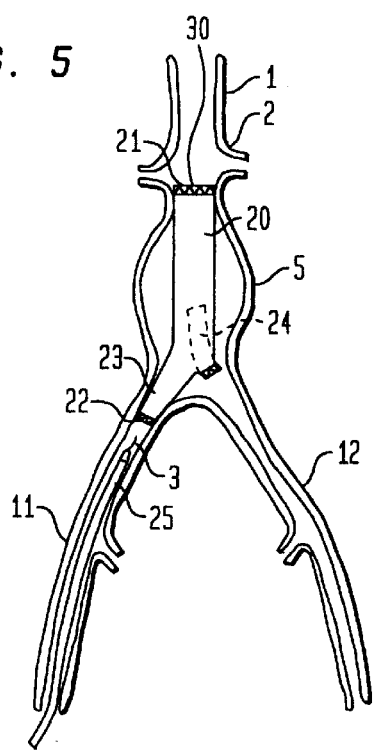

Referring to FIG. 5, the graft 20 is shown expanded and deployed between the thoracic artery 1 and the right iliac artery 11. Stent 21 has enlarged (or been enlarged) to engage the interior wall of the thoracic artery 1 and hold the graft 20 in place. The second stent 22 is shown engaging the right iliac artery 11 to hold left leg 23 in place. With the delivery mechanism illustrated in FIG. 4, the graft 20 has been delivered with the stents 21 and 22 in place within graft 20. The right leg 24 of the graft has been inverted within the graft 20 during the delivery. When the stents are deployed, the right leg 24 will remain inside of the graft 20. Following deployment of the graft 20, the guidewire 10 and center shaft 25 (upon which the graft 20 was mounted when the device was deployed within the artery) is withdrawn through the right iliac artery 11.

Figure 6:
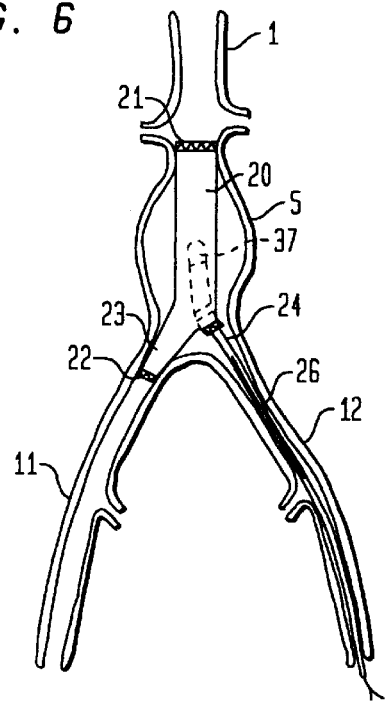

As shown in FIG. 6, a catheter 26 is inserted into the left iliac artery 12 and directed into right leg 24 that is inverted in the graft 20. One of the more suitable means for engaging the leg 24 is a catheter carrying a balloon 37 with a stent mounted upon it (if the leg 24 was not implanted with a stent already in place) Enlargement of the balloon 37 will enlarge the stent sufficiently to enable the stent to grasp the inside of the leg 24 and withdraw it through itself. Alternatively, a catheter with a stent mounted on it can be inserted into the leg 24 after it has been drawn into the left iliac artery 12. Another mechanism to withdraw the leg is to insert a hook which will engage the inverted leg. The stent can be enlarged as described above.

Figure 7:
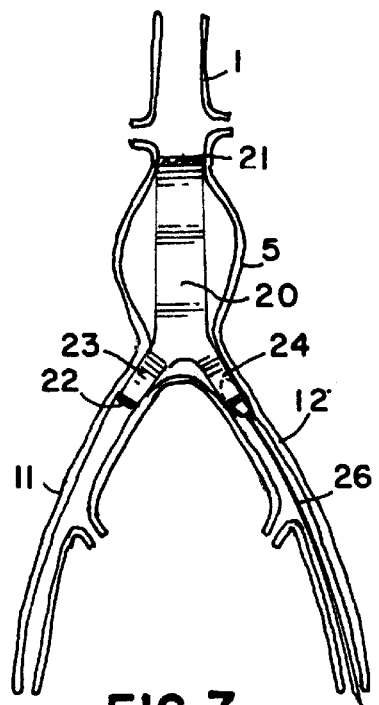

As shown in FIG. 7, the catheter 26 that was inserted into the left iliac artery 12 to engage the distal open end of the leg 24 is being withdrawn from within the graft 20 by drawing catheter 26 through the artery 12. The distal open end and the inverted leg 24 will follow it. When the inverted leg 24 is fully withdrawn, one of several techniques can be used to implant the stent. In one technique, the stent is deployed upon a balloon catheter and inflation of the balloon (when the stent is in a correct position in the left iliac artery 12) will cause the stent to be seated. Another approach involves a stent disposed within the leg 24 while it is inverted within the graft 20. In this approach, when the leg 24 is drawn from the graft 20 the stent will emerge and enlarge automatically as the leg 24 is drawn out. Moreover the stent can be a polymeric impregnation of the leg, as mentioned above. Expansion of the leg 24 against the artery and heating will stiffen the leg 24 to implant the prosthesis.

Figure 8:
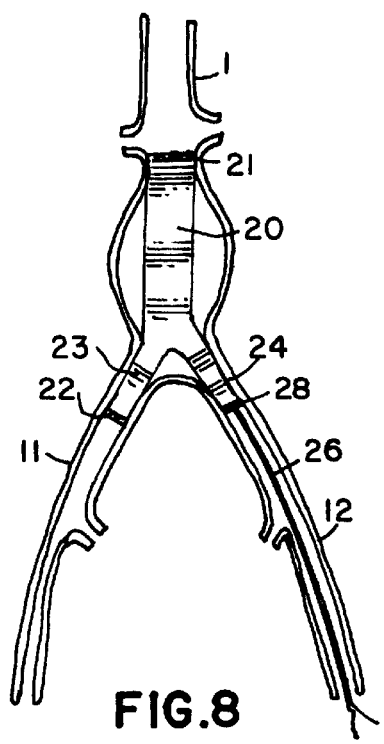
Figure 9:
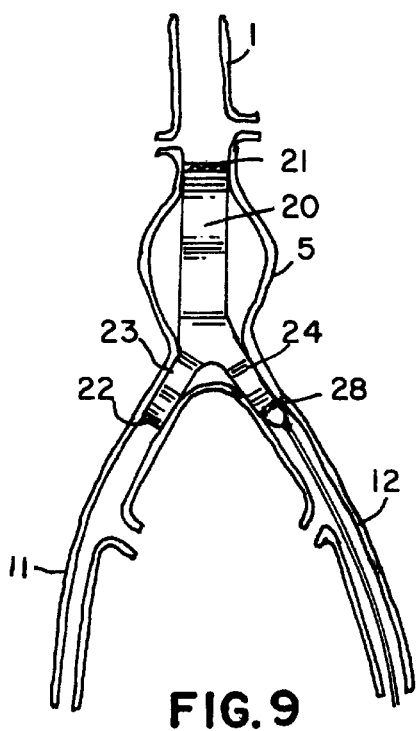

In FIG. 8 the balloon catheter is shown enlarging the stent to it in the iliac artery 12. FIG. 9 shows the balloon catheter being moved from the position within the stent 28 just immediately prior to withdrawal of the catheter 26 from the iliac artery. The balloon can be deflated to allow for easy withdrawal of the catheter from the stent and through the artery.

Figure 10:
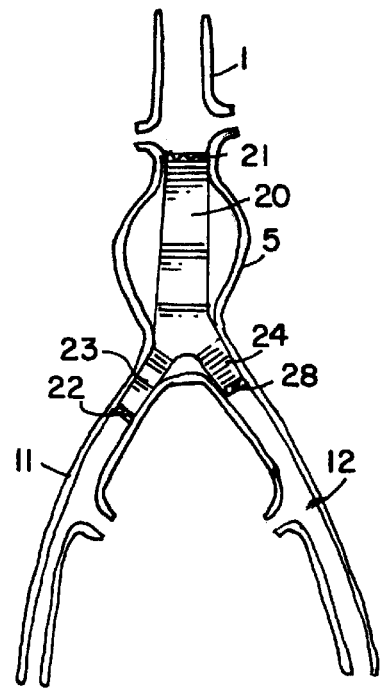

FIG. 10 shows the graft 20 implanted between the two iliac arteries 11 and 12 and the thoracic aorta 1. A stent 22 anchors the left leg 23 of the graft 20 to the right iliac artery 11 and a stent 28 anchors the right leg 24 to the left iliac artery 12. The aneurysm 5 surrounds the graft but does not receive blood into it. Drainage of the aneurysm can be accomplished percutaneously or otherwise, as is conventional.

The graft depicted in FIG. 2 of the drawings having only one distal open end can be deployed and implanted similarly as the embodiment shown in FIG. 1, except the procedure is less complicated in that the procedure requires entering through only one of the iliac arteries.

While it is apparent that changes and modifications can be made within the spirit and scope of the present invention, it is my intention, however, only to be limited by the appended claims.

As my invention I claim:

1. An intraluminal device comprising a graft and at least a first stent for anchoring at least one end of the graft within a body lumen, the device comprising a body portion and at least one branch portion connected to the body portion, the branch portion adapted to be inverted within the body portion during insertion into a body lumen and to be withdrawn from the body portion after insertion of the device in the body lumen.

2. The intraluminal device of claim 1, wherein the at least one branch portion comprises a plurality of branch portions adapted to be inverted.

3. The intraluminal device of claim 2, wherein the body portion comprises a proximal portion and the plurality of branch portions adapted to be inverted comprises a first distal leg portion and a second distal leg portion.

4. The intraluminal device of claim 3, wherein the body portion is adapted for insertion in an aorta, the first distal leg portion is adapted for insertion in a first iliac artery, and the second distal leg portion is adapted for insertion in a second iliac artery.

5. The intraluminal device of claim 1, wherein the body portion comprises a proximal portion and a first distal leg portion, and the at least one branch portion adapted to be inverted comprises a second distal leg portion.

6. The intraluminal device of claim 5 further comprising a second stent for anchoring a distal end of the first distal leg portion.

7. The intraluminal device of claim 5, wherein the body portion is adapted for insertion in an aorta, the first distal leg portion is adapted for insertion in a first iliac artery, and the second distal leg portion is adapted for insertion in a second iliac artery.

8. The intraluminal device of claim 2, wherein the at least one branch portion is adapted to be inverted a first time to form a first cuff within the body portion and a second time to form a second cuff within the first cuff.

9. The intraluminal device of claim 2, wherein the at least one branch portion is tapered.

10. The intraluminal device of claim 2 comprising a proximal open end and at least a first distal open end, wherein the at least one stent comprises a proximal stent portion disposed within and attached to at least a proximal portion of the device including at the proximal open end.

11. The intraluminal device of claim 10, wherein the at least one stent further comprises a first distal stent portion disposed within and attached to at least a first distal portion of the device including at the first distal open end.

12. The intraluminal device of claim 11, wherein the proximal stent portion protrudes proximally from said proximal open end and the first distal stent portion protrudes distally from the distal open end.

13. The intraluminal device of claim 11, wherein the proximal stent portion and the first distal stent portion comprise self-expanding stent portions.

14. The intraluminal device of claim 10, wherein the device comprises a second distal open end located at a distal end of the branch portion and the at least one stent further comprises a second distal stent portion disposed in and attached to a distal portion of said branch portion including at the second distal open end.

15. The intraluminal device of claim 14, wherein the at least one stent comprises a single, integral stent extending from the proximal open end to the first distal open end and the second distal open end.

16. The intraluminal device of claim 14, wherein the proximal stent portion and the first distal stent portion comprise self-expanding stent portions.

17. The intraluminal device of claim 16, wherein the second distal stent portion comprises a self-expanding stent portion.

18. The intraluminal device of claim 16, wherein the device comprises a second distal open end located at a distal end of the branch portion, in which the branch portion is unsupported by a stent portion until after introduction into the body lumen.

19. The intraluminal device of claim 16, wherein the at least one stent comprises a single, integral stent extending from the proximal open end to the first open end.

20. The intraluminal device of claim 1, wherein the at least one stent is expandable from a first narrow diameter to a second wider diameter.

21. The intraluminal device of claim 1, wherein the at least one stent comprises a self-expanding stent.

22. A method of inserting an intraluminal device comprising a graft and at least a first stent for anchoring at least one end of the graft within a body lumen, the device comprising a body portion and at least one branch portion connected to the body portion, the method comprising the steps of:

inverting the at least one branch portion within the body portion;

inserting the intraluminal device into a body lumen; and pulling the at least one branch portion out of the body portion of the device while inside the body lumen.

23. The method of claim 22, wherein the pulling step comprises inserting a hook into the inverted branch portion and pulling.

24. The method of claim 22, wherein the pulling step comprises engaging the inverted branch portion using an inflatable balloon.

25. The method of claim 22, wherein the pulling step comprises engaging the inverted branch portion with a stent mounted on an inflatable balloon.

26. The method of claim 22 wherein the at least one branch portion of the intraluminal device comprises a plurality of branch portions adapted to be inverted, and the method comprises inverting each of the plurality of branch portions prior to inserting the intraluminal device into the body lumen, and then pulling each of the plurality of branch portions out of the body portion of the device while inside the body lumen.

27. The method of claim 26, wherein the body portion comprises a proximal portion and the plurality of branch portions adapted to be inverted comprise a first distal leg portion and a second distal leg portion, the method comprising inserting the proximal portion in an aorta, and then pulling the first distal leg portion into a first iliac artery, and pulling the second distal leg portion into a second iliac artery.

28. The method of claim 22, wherein the body portion comprises a proximal portion and a first distal leg portion, and the at least one branch portion adapted to be inverted comprises a second distal leg portion, the method comprising inserting the proximal portion in an aorta with the first distal leg portion in a first iliac artery, and then pulling the second distal leg portion into a second iliac artery.

29. The method of claim 22, wherein the pulling step comprises engaging the inverted branch portion and a stent portion in the inverted branch portion self-expanding from a compressed configuration to an expanded configuration.

* * * * *